United States Patent [19]

Schneider et al.

[11] 4,156,681

[45] May 29, 1979

[54] PROCESS FOR ISOLATING ALBUMIN FROM BLOOD

[75] Inventors: Waldemar Schneider; Christian Fröhlich, both of Hagen; Harald Fiedler; Hans Lefevre, both of Munster, all of Fed. Rep. of Germany

[73] Assignee: Plasmesco AG, Zug, Switzerland

[21] Appl. No.: 755,126

[22] Filed: Dec. 28, 1976

Related U.S. Application Data

[63] Continuation-in-part of Ser. No. 561,868, Mar. 25, 1975, abandoned.

[30] Foreign Application Priority Data

Mar. 28, 1974 [DE] Fed. Rep. of Germany ....... 2415079

[51] Int. Cl.$^2$ ............................................. A23J 1/06
[52] U.S. Cl. ................................ 260/122; 260/112 B; 260/121
[58] Field of Search .................... 260/112 B, 121, 122

[56] References Cited

U.S. PATENT DOCUMENTS

| | | | |
|---|---|---|---|
| 2,705,230 | 3/1955 | Reid | 260/122 |
| 2,710,293 | 6/1955 | Gerlough | 260/122 |
| 2,710,294 | 6/1955 | Gerlough | 260/122 |
| 2,761,808 | 9/1956 | Singher | 260/112 B |
| 2,765,299 | 10/1956 | Porsche | 260/122 |
| 3,361,732 | 1/1968 | Dazey | 260/112 B |
| 3,497,492 | 2/1970 | Buck | 260/122 |
| 3,763,135 | 10/1973 | Shambrom | 260/112 B |
| 3,808,189 | 4/1974 | Breuer | 260/112 B |
| 3,926,939 | 12/1975 | Ivanov | 260/122 |

OTHER PUBLICATIONS

Saint-Blancard, *Chem. Abstracts,* vol. 81:61,604u (1973).
Carrera, *Chem. Abstracts,* vol. 62:8949a (1964).
Jimenez, *Chem. Abstracts,* vol. 82:40,432s (1974).
Albinsson, *Chem. Abstracts,* vol. 76:82,575x (1971).

*Primary Examiner*—Walter C. Danison
*Attorney, Agent, or Firm*—Cushman, Darby & Cushman

[57] ABSTRACT

Method for the abstraction of pure serum albumin from blood which includes the steps of separating the blood plasma from the solid constituents of the blood and isolating the dissolved non-albumin constituents from plasma, adding an albumin-stabilizer and treating such fluid with a lower aliphatic alcohol, whereby, the treatment is carried out at a volume concentration of alcohol of 7 to 14% in the presence of 0.001 to 0.1 moles of the stabilizer, at a temperature of from 60° to 75° C. and pH of from 4.5 to 7.5; the concomitant proteins, partly or largely denatured, are precipitated; the resultant solution containing pure serum albumin is separated from the precipitate at a temperature of from 1° to 30° C., preferably at room temperature.

12 Claims, 11 Drawing Figures

PROCESS FOR ISOLATING ALBUMIN FROM BLOOD

The present application is a continuation-in-part application of U.S. Ser. No. 561,868, filed Mar. 25, 1975 and now abandoned.

This invention relates to the recovery and isolation of serum or blood albumin, from blood, blood products, other body fluids or tissue extracts, for use in the therapy applied to men.

To replace the less effective and more dangerous treatment with stored whole blood, component therapy is coming into its own in modern medicine. In addition to being waste of the basic material, whole blood has the highest risk of causing transfusion reactions, immunizations, and disease transfer, particularly hepatitis. By administering blood components these risks are either completely avoided (e.g. human serum albumin) or diminished (e.g. buffycoat free packed red cells).

So in recent years, the separation and concentration of blood protein fractions has been of interest for a variety of uses. Blood is a fluid which consists of solid and liquid constituents. The solid constituents include red and white blood corpuscles and blood platelets. The plasma or liquid part of the blood contains about 90% of water and 10% of solids. The substance dissolved in the plasma include, inter alia, albumin, which is the sole protein constituent of plasma which ist stable to temperatures in excess of about 60° C. It is in itself known to separate the blood plasma from the red and white blood corpuscles and from the blood platelets. Furthermore it is known to remove gammaglobulins as well as coagulation-promoting substances, such as, for example, fibrinogen, from the plasma. For therapeutic or diagnostic purposes it is desirable to obtain as pure an albumin solution or albumin paste as possible, which should, as far as possible, not contain any further protein constituents of the blood plasma.

In the past, the separation of albumin from protein and other components of human plasma has been accomplished by control of the relative solubilities of the components of the plasma. This conce pt is used by a process known as COHN-method. The CONH-method was developed in 1946, (J. Am. Chem. Soc. 68 (1946) p. 459 ... 475) and got world-wide acceptance for the technical fractionation of plasma proteins to be used for human therapy. Human plasma is separated into five fractions by using different concentrations of ethanol, employed as a non-toxic protein precipitant, while simultaneously changing the pH with buffers of different ionic strength. The concentration of alcohol increases from about 8% to 40%, the pH varies from 7.2 to 4.6. The ethanol can subsequently be easily removed by freeze-drying, but the disadvantage lies in the fact, that it readily denatures proteins, especially when used in high concentrations.

This disadvantage may be reduced by lowering the temperature to between −3° and −7° C. during fractionation. To accomplish this for large scale fractionation, either the entire process must take place in a cold room (an uncomfortable und unhealthy situation for the personnel), or self-cooling machinery must be used. In addition to this, all electrical equipment must be specially protected when working with large volumes of alcohol.

The first COHN fractionation step removes mainly fibrinogen (Fract. I); the second-third, gammaglobulin (Fract. II–III); the fourth alpha-and-beta-globulins (Fract. IV). The remaining supernatant contains albumin which is precipitated with 40% ethanol as Fract. V. An additional purifying precipitation is required if high albumin concentrations (20%) are desired (Fract. VI).

Fract. V albumin paste (crude or refined) must be lyophilized to remove the ethanol. The powder is solved, the solution is cleared through filtration, and the pH, osmolality, and protein concentration are adjusted. Also, aliphatic carbonic acids (e.g. caprylic acid) must be added to protect the protein from heat denaturation during pasteurization. Caprylic acid is most often used for stabilization usually in concentrations between 0.004 M (5% albumin) and 0.04 M (20% albumin).

Generally speaking, the five-steps COHN-method isolates four useless fractions, thus making production of the fifth, albumin, unnecessarily expensive.

Consequently, less expensive methods for albumin fractionation have been looked for. In particular achieving a situation is desirable, where the working time ist shortened, the number of working steps is reduced, the nuisance to personnel is limited and the purity is increased without lowering the yield. In addition it is also desirable that the technical effort required should be substantially reduced.

It is known for the recovery of serum or blood albumin from the whole blood, plasma, or serum of cattle, hogs, and sheep (mammalians), by the steps of selectively denaturing and coagulating other protein constituents than albumin by heating said solution to a temperature of about 45° C. to 75° C., while said solution contains about 0.0075 to 0.02 mol concentration of caprylate ions, and then separating the coagulum of said other protein constituents from the supernatant solution of said serum albumin. In the process according to the invention no alcohol is used. Only for precipitating the albumin after the heating process, alcohol (ethanol) can be used to a concentration of 40%. The precipitated albumin paste is lyophilized and the dry powder processed anew.

Apparently due to the lack of a sufficient alcohol concentration during the heating process in connection with the relatively high concentration of caprylate ions, the standard of purity in this process is too low. The percentage of albumin recovered lies between 90 and 96% in the whole dry powder. The minimum albumin content of Normal Serum Albumin (Human) for therapeutic purposes is 96% of the total protein according to current FDA regulations.

Because some of the preliminary steps may be carried out at low temperatures and an alcohol content of 4%, residues of this alcohol may be left in the aequous solution of the serum albumin. The presence of 4% alcohol in the solution does not interfere in the process. On the other hand, this amount of alcohol is not enough to gain the desired 100% precipitation of globulins.

Further, in U.S. Pat. No. 3,926,939 (Ivanov et al.) a method for extracting pure serum albumin from biological fluids is known, which comprices treating such fluids with a lower aliphatic alcohol and a salt of a carboxylid acid, whereby the treatment is carried out at a volume concentration of alcohol of 15 to 33% in an presence of 0,1 to 0,6% of the aliphatic carboxylate having in non-toxicication and an anion comprising from 6 to 12 carbon atoms at a temperature of from 1° to 30° C. and pH of from 2 to 5, the concomitant proteins being partly or largely denatured, depending on the pH value selected for the process; the denatured and native concomitant proteins are precipitated at a pH value of from 4 to 5 and at a temperature of from 1° to 30° C., with the non-protein impurites which form complexes with the albumin being split off therefrom and adsorbed by the precipate; the resultant solution containing pure serum albumin is separated from the precipitate at a temperature of from 1° to 30° C. and pH of from 4 to 5.

Experiments show that with the method mentioned the yield of serum albumin is comparatively low, especially when the purity to be achieved is high (more than 99%). At optimal conditions, only about 55% yield is achieved, compared to the theoretical achievable amount of 100%. In addition, the high alcohol content in the solution of more than 15% is difficult to remove, resulting in high costs of purification.

It ist therefore a general object of the invention to provide a commercially feasible process for the recovery of serum albumin from the other protein constituents of human blood or other suitable fluids.

It is a further object of this invention to provide such process which is applicable to the direct recovery of serum albumin from the plasma with high percentage of yield, high purity making the product applicable to the human body, even for intravenous application. It is a further object of this invention, to provide this method not only for the extraction of pure serum albumin from donor blood, but also from various forms of raw materials, such as haemolized blood plasma, placental sera and placental extract.

In accordance with the object of the invention, there is provided a method for the extraction of pure serum albumin from said fluids, which includes separating the plasma from the solid constituents of the blood (e.g. blood cells and blood platelets) and isolating the dissolved non-albumin-constituents from blood plasma, adding an albumin-stabiliser, e.g. non-toxic salt of a carboxylic acid, and treating such fluid with a lower aliphatic alcohol having the composition $CH_3-n(CH_2)-OH$, with n=0,1 or 2, whereby, in accordance to the invention, the treatment is carried out at a volume concentration of the alcohol of 7 to 14% in the presence of 0.001 to 0.01 moles of the stabiliser, at a temperature of from 60° to 75° C. and pH of from 4.5 to 7.5; the concomitant proteins, partly or largely denatured, are precipitated; the resultant solution containing pure serum albumin is separated from the precipitate at a temperature of from 1° to 30° C., preferably at room temperature.

The alcohol is preferably ethanol taken to the extent of 8 to 12% by volume; the preferred carboxylic acid is sodium caprylate in a 0.004 mol concentration. The preferred pH value of the treatment is 6 to 7 and the preferred temperature is 67° to 69° C.

The following table shows, that at a temperature of 68° C. and a pH-value of 6,5 a maximum yield of 96% albumin (according to 100% content in a human blood plasma) may be achieved from said plasma. The table also shows, that it may be possible to work within a certain range of alcohol contents without leaving the scope of the invention.

Table (yield of albumin, when treating human blood plasma at 68° C. and pH = 6.5; 0,004 mol sodium-caprylate at different alcohol contents)

| yield of albumin (%) | alcohol content (% by volume) |
| --- | --- |
| .} *) | 5,0 |

Table-continued (yield of albumin, when treating human blood plasma at 68° C. and pH = 6.5; 0,004 mol sodium-caprylate at different alcohol contents)

| yield of albumin (%) | alcohol content (% by volume) |
| --- | --- |
|  | 6,0 |
| 88 | 7,0 |
| 89 | 8,0 |
| 96 | 9,0 |
| 92 | 10,0 |
| 90 | 11,0 |
| 82 | 12,0 |
| 75 | 13,0 |
| 68 | 14,0 |
| 63 | 15,0 |

*With a concentration of alcohol lower than 8% the separation of gamma globulin from albumin is not complete, as demanded by FDA regulations. Therefore the albumin is not applicable.

Other series of tests show similar results. The optimum of alcohol content lies at about 9% for similar conditions.

Known in the art are the mentioned protein- and albumin-stabilisers, which even at heating of a pure albumin-solution up to 60° C. will prevent any visual alteration of the albumin. The work of BALLOU et al. (J. Clinical Invest. 23 (1944); pp 454; J. Biol. Chem. 153 (1944); pp. 589) hint, that sodium-salts of propionate, butyrate, valerate, caproate, caprylate phenylacetate and phenylbutyrate have the desired stabilising property.

As a result the concomitant proteins are being precipitated at about 68° C., while the albumin is staying in solution in the presence of alcohol and stabilisers. It is possible to dispense with cooling during the separation. In addition, numerous working steps are saved, since fractional precipitation is dispensed with. Instead, all globulins can be removed in one working step.

An advantage over the known process proposed by Ivanov et al. (U.S. Pat. No. 3,926,939) is, that a higher yield is achieved by using a lower alcohol content, which is easier to remove.

A temperature of 68° C.±3° C. has proved to be the optimum working temperature for precipitating the unwanted proteins in the presence of sodium caprylate and ethyl alcohol.

Surprisingly, heating up to this temperature does not cause irreversible denaturation changes in the albumin, as predicted by Ivanov et al. (U.S. Pat. No. 3,926,939). In the contrary, immuno-electrophoresis and other tests show, that the biophysical properties of the albumin rendered are the same of any untreated albumin.

Normally, the supernatant fluid containing the albumin is separated from the concomitant proteins by a centrifugation process, for example at a temperature of 28° C. and at a pH of 4.4. The precipitated proteins are sedimented in the rotors while the albumin remains in the supernatant as an approximately 2.5% solution. This supernatant is collected from the centrifuges in separate containers. The yield at this point in the process ist about 70% of the albumin available in the original plasma. By eluting the sediment with distilled water at pH 4.8 and recentrifuging, another 20% albumin can be recovered.

Therefore, with this method it is a disadvantage, that a relative high amount of albumin will remain in the sediment, so that one or more eluting steps are necessary. In addition, the centrifugation steps are very time consuming. In spite of these disadvantages, no other process has until now been considered, because it is necessary with the COHN-method to use centrifugation steps. Tests proved, that the suspension mentioned above practically could not be filtered economically.

Contrary to experience and expectation, surprisingly there can be solved the object of separating the thermally precipitated proteins from the suspension with substantially low expenditure, by performing such separation by alluvial filtration of the suspension in accordance with the present invention.

Alluvial filtration is known per se. Normally, alluvial filtration is performed in centrifugal purification filters comprising essentially a closed pressure vessel wherein circular filter elements are disposed on a centrally rotating hollow shaft, which filter elements are positioned either horizontally or in vertical position in parallel with each other. Customarily, the filter elements are fitted with a metallic twist (wire) or braid fabric.

The substance to be filtered is admixed with filtering aids, normally kieselguhrs or diatomites, which are added to the substance in metered fashion in accordance with the type or turbidity and with the character of the residues.

The filtrate collected on the filter elements is floated away by rotation of the filter elements and countercurrent flushing. The residues are discharged as a so-called slurry.

In the present instances, the alluvial filtration offers surprising advantages, since other types of filters and other filtrations methods require filtering periods of such a length that no advantages are obtained at all over the time consuming centrifuging method. Hereby, the following filtering methods have been tested: Purifying filtration by means of carbon and asbestos plate filters; filter layers on the basis of cellulose; fiberglass filters; sintered glass. The filtering methods employed resulted either in excessive filtering periods, in clogging of the filter inserts (elements), or in turbid filtered liquids. It is only the use of a alluvial filter that allows to obtain clear filtrates which do not require any additional clarification or purification filtration and which, thus, permit optimum performance of the operations in the recovery of albumin to be obtained.

In particular, it is proposed that the filtration is performed within a centrifugal purification filter comprising a closed (sealed) pressure vessel, and with a mesh size of the filter elements of between 20 and 200 microns.

More particularly, the liquids in question are processed at a mesh size of from 70 to 90 microns. This mesh size provides an optimum between the throughflow that can be obtained and complete filtering out, in which case a single filtering step only is required to be carried out in each operation.

In order to adequately prepare the filter surface for the subsequent filtrations, it is expedient in some instances initially to perform a primary precoating with a neutral liquid wherein the filter element is precoated with a layer of the filtering aid having a thickness of about 0.5 centimeters. As filtering aids, the customary, commercially available kieselguhrs sold under the tradenames Hyflo-Super-Cel, Celite 545 or perlite are suitable. Additionally, cellulose filtering aids of conventional type are also useful, although with lesser filtering efficiency. These filtering aids likewise allow to obtain a product being satisfactory for many applications. It is recommendable that the filtering aid is subjected to preswelling or pre-soaking.

Favorable filtering effects are obtained with a horizontally disposed filter element of metallic twist (wire) or braid fabric having a mesh size of 80 microns.

A favorable compositon compromises a suspension of from about 4 to 6% of plasmatic protein, to which suspension there are added from about 20 to 70 grams of kieselguhr filtering aid per liter. Thereafter, this suspension is filtered. Lower concentrations of protein may require lesser quantities of filtering aids under certain circumstances.

In order to recover also the albumin present within the slurry or turbid volume, it is proposed that this albumin is likewise isolated by means of a residual volume filtering device comprising a small portion of the total filter area, after a cleaning by rotation and countercurrent flushing or a clearing of the volume of the filtering apparatus place in a recirculation system has been performed.

For enriching of the albumin from the residual albumin-containing fluid, maleic acid or polyethylene glycol are known in the art to be of particular usefulness as precipitating media; however, it is also possible to use for this concentration step still other polymerized, aliphatic multivalent alcohols, organic acids, specific salts, monomeric alcohols, or other methods suitable for protein (albumin) concentration.

In order to convert the precipitated albumin paste into a solution of the desired concentration, the paste ist dissolved—following the abovementioned steps—in a preferably bufferd liquid. The albumin solution can the preferably be heat-sterilised, without adding a stabiliser.

Variants of the process sequence and further features and advantages of the new process are illustrated with the aid of the drawing. In the figures:

FIG. 1a shows the precipitation process according to the so-called Cohn method;

FIG. 1b schematically shows the new process; and

Figures 1A, 1B:
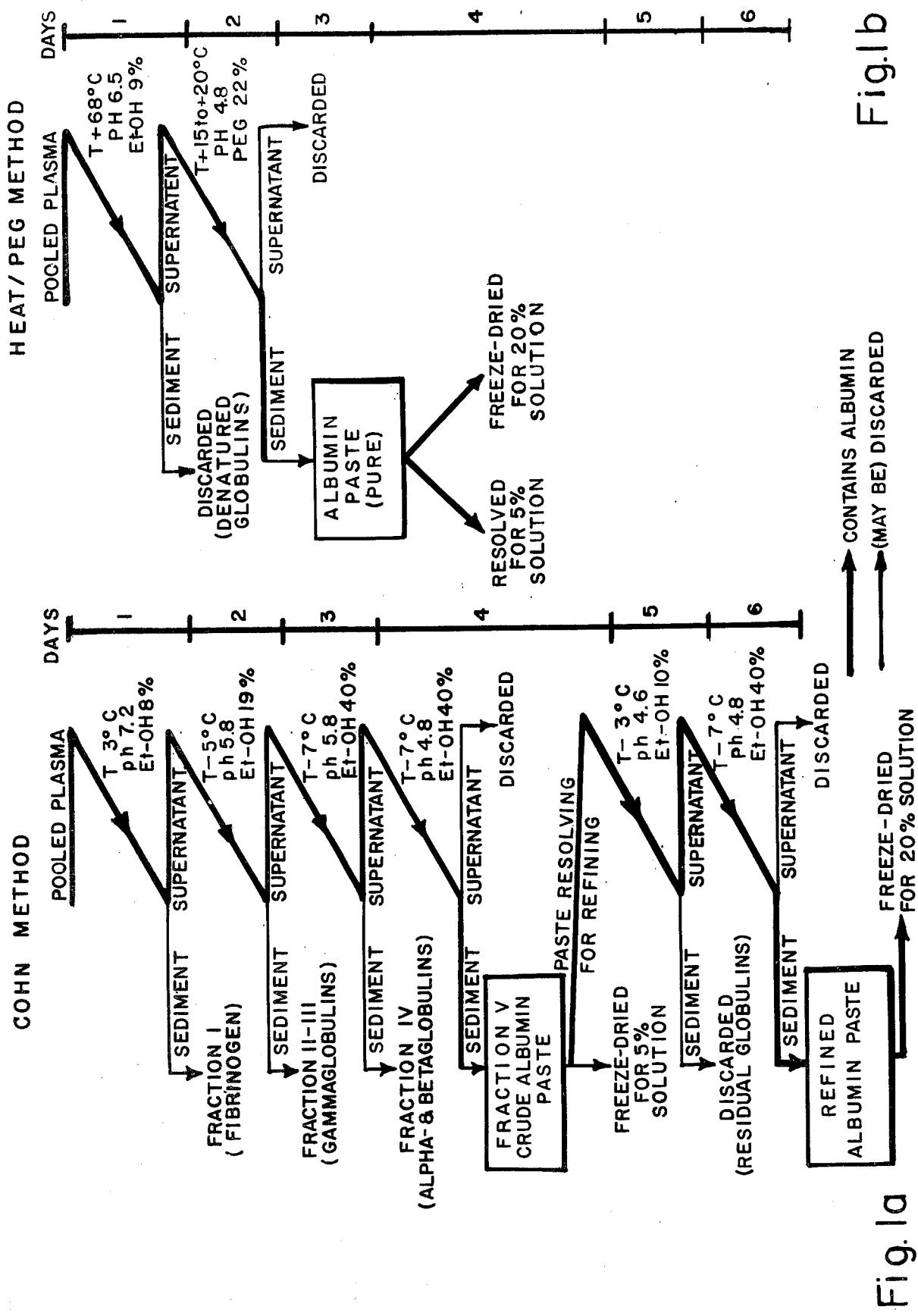

FIG. 1a schematically shows, in stages, the process of the so-called Cohn method. This starts from a mixed plasma to which 8% of ethanol is added and which is precipitated at a pH value of 7.2 and at minus 3° C. This results in fraction I separating out. The ethanol content of the supernatant liquid is then increased to 19% at minus 5° C. and a pH value of 5.8. This causes fraction II/III, which in the main consists of gamma-globulins, to separate out. The supernatant liquid is again treated at a higher alcohol content, at a pH value of 5.8 and at a temperature of minus 7° C. This gives fraction IV, consisting in the main of alpha- and beta-globulins. The supernatant liquid is subjected to a further treatment, at a pH value of 4.8 and a temperature of minus 7° C. (ethanol content 40%). Hereupon, the so-called crude albumin separates out as a sediment. The supernatant liquid is discarded. After freeze-drying to remove the alcohol, the crude albumin can be taken up in, or converted into, a 5% strength solution. However, it is also possible again to take up the crude albumin paste and convert it into a purified albumin paste in two further steps (for which the conditions can be seen from the diagram).

In total, about 6–8 days are required for the preparation of the purified paste if a normal 8 hour day ist worked. Furthermore, very careful cooling is required, which demands correspondingly high expenditure on technological apparatus.

In contrast, the new process can be carried out substantially more simply (see FIG. 1b). Here again, a mixed plasma or other fluids containing albumin and globulin are used as the starting material; it is first subjected to a heat treatment at a temperature of 68° C. in the presence of aliphatic, lowmolecular alcohols and of stabilisers. Suitable stabilisers are, as mentioned, certain aliphatic carboxylic acids and their salts, such as say, sodium caprylate, and other constituents.

In this first process step, which is carried out at a pH value of 6.5 and an ethanol content of 5 to 12%, all globulins are denatured and separated out as a sediment. After cooling, the supernatant liquid is acidified to pH 4.8 and a precipitation medium, such as, say, 22% of polyehtylene glycol (PEG), or 18% maleic acid, is added. After an appropriate reaction time, a very pure albumin paste separates out and this is either freeze-dried or taken up to form a 5% strength solution.

Figure 2:
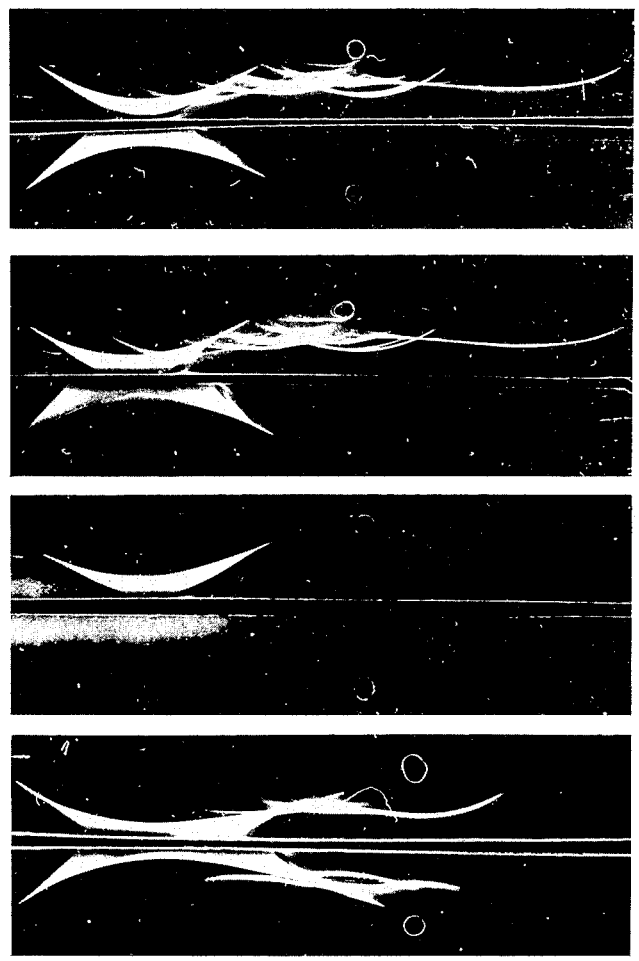
FIG. 2a–2h show immuno-electrophoresis diagrams (IEP) of different albumin preparations produced in accordance with known processes or in accordance with the new process.
Figure 3:
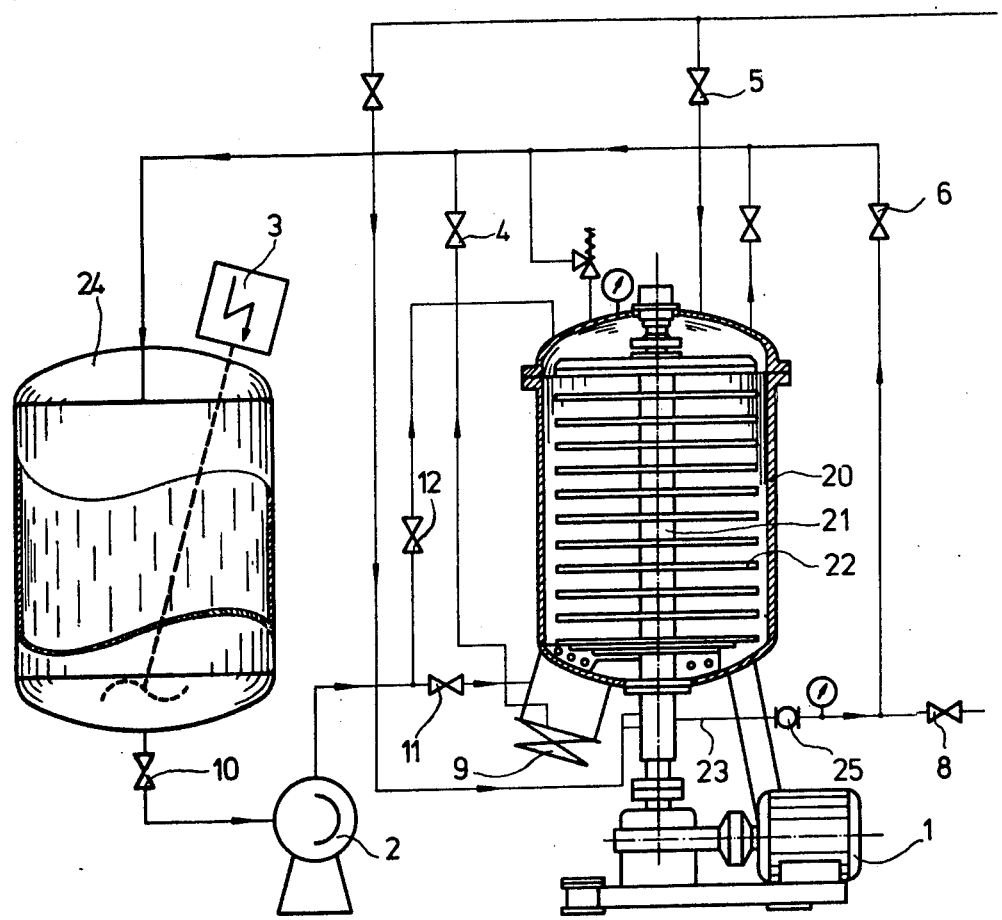
FIG. 3 shows a system for filtering the albumin-containing supernatant.

As can be seen from the basic descriptions, the new process requires a substantially shorter time and substantially less technological effort. In addition, however, the albumin obtained is also substantially purer than that obtained according to known methods. FIGS. 2a to 2h show immuno-electrophoresis diagrams (IEP), from which the following can be discerned:

FIGS. 2a and c show IEP diagrams of a natural plasma, in which the sickle-shaped mark of albumin is formed on the left; the thinner sickle-shaped marks which follow on the right originate from globulins which must be regarded as impurities in an "pure" albumin solution. Albumin solutions prepared according to a known process are shown in FIGS. 2g and h. It can be seen clearly that a part of the impurities has been removed; however, far from all the undesired protein constituents have been removed.

FIGS. 2b and d show albumin solutions which have been obtained in accordance with the new process. Here, almost 100% purity is achievable.

FIG. 2f shows the supernatant liquid which was obtained after the last process step (precipitation of the albumin). It can be seen that this liquid virtually no longer contains any albumin. It follows that the first process step (heating to 68° C. in the presence of alcohol and sodium caprylate) already achieves practically complete separation of albumins and other proteins of the plasma.

EXAMPLE 1

The starting material ist pooled donor plasma, from which the coagulation factors have been removed. The coagulation factor VIII and the fibrinogen have been removed by cryoethanol sedimentation. The prothrombin complex is removed by DEAE-cellulose adsorption. The original plasma is Hepatitis-B$_5$-antigen negative, has normal transaminase values and does not contain any visible haemoglobin.

Sodium caprylate is added to the plasma until the concentration is 0.004 molar. The mixture is heated in a stainless container within 3 hours to 68° C., heat being supplied at an even rate. At the beginning of the heating, the concentration of ethanol is brought to 9% by volume, and the pH value is set to 6.5, which is obtained by adding 0.5 n HCl. The plasma is continually stirred during the heating process.

When a plasma temperature of 68° C. is reached, the plasma is transferred by compressed air into a container which is connected to a cooling system. The plasma is stirred until the temperature ist brought down to +10° C. (about 4 hours), at which time the pH is lowered to 4.4 with 0.5 n HCl. The acidified plasma is now left to stand overnight at about 10° C. During this time the unwanted proteins coagulate. The pure albumin stays dissolved in the fluid.

The fluid with the sediments is pumped into continuous flow centrifuges through silicone tubes, where it is separated by centrifugation. The proteins which have separated out collect in the rotors and the albumin remains in the supernatant liquid. The proteins which have separated out in the rotors still contain albumin, which can be isolated additionally by reeluting and renewed centrifuging.

The temperature may be changed in the range of 65° C. . . . 75° C., Whereas the alcohol content may change from 7 . . . 12%. The table already mentioned includes the relation between alcohol content and albumin recovery at pH=6.5 and 68° C. temperature, using the conditions of example 1.

As may be seen, the maximum of recovery lays at 9%. A lower or higher content result in worsening of purity and/or yield of the albumin.

The supernatant liquid is filtered through so-called SSK filters (Seitz, Bad Kreuznach, Germany) to remove remaining lipids and modified proteins. To the clear fluid a precipitant is then added, preferably maleic acid or polyethylene glycol in a concentration of 18% to 22% at room temperature. The albumin precipitates.

The albumin suspension is again centrifuged. This leaves the polyethylene glycol and the salts in the protein-free liquid. The albumin collects as a paste in the rotors. It is taken up in distilled water in a container, and converted into a solution of approx. 8% strength. After a clarifying filtration, the albumin can be converted directly into a 4–5% strength solution for use, the osmolality (osmotically measured molar strength) being adjusted with glucose or other suitable substances. The product is then sterile-filtered, filled into bottles and pasteurised for at least 10 hours at 60° C.

Also, the supernatant liquid may be filtered through SSK filters in order to remove remaining lipids and modified proteins. Then, polyethylene glycol having a molecular weight of from about 4000 to 6000 is added as the precipitating agent in a concentration of 22% at room temperature. The albumin precipitates within a period of 30 minutes. The albumin suspension is centrifuged again. Hereby, the polyethylene glycol and the salts are retained in the protein-free liquid. The albumin is collected as a paste in the rotors. The albumin is redissolved in a container in distilled water and converted into an about 8% solution. After a clarifying filtration, the 8% albumin is freeze-dried. The dried powder is dissolved in distilled water, whereby the osmolality—as explained in Example 1—may be adjusted, if desired.

EXAMPLE 2

The starting material is a placental serum. After the globulin have been removed by known methods, the concentration of ethanol in the solution is brought to 8.2% by volume, and sodium caprylate is added until its concentration is 0.005 mol. Then the pH is set to 6.0, which is obtained by adding 0.5 n HCl. Then the mixture is heated evenly in 150 minutes up to 65° C. The mixture is continually stirred during the heating process.

After reaching this temperature, the mixture is held for 30 minutes. Then the mixture is transferred and cooled down to 20° C. and the pH is lowered down to 4.5. The acidified plasma is now left to stand for three hours to let coagulate the unwanted proteins. The solution containing pure albumin is separated from the resultant precipitate at a temperature of 20° C. and pH 4.5 by centrifugation.

The albumin in the supernatant may be separated as mentioned in Example 1, e.g. by precipitation with PEG.

EXAMPLE 3

The solid constituents (blood cells and blood platelets) are separated from human blood, and the coagulation factors are removed. The starting solution contains from about 5 to 6% of plasmatic protein. In accordance with the process disclosed in the above publication, the clotting factor VIII and the fibrinogen are removed by cryo ethanol sedimentation. The prothrombin complex is removed by absorption. The original plasma is Hepatitis-$B_5$-antigen negative, it shows normal transaminase values, and it does not contain any visible haemoglobin. Sodium caprylate is added to the original plasma until a concentration of 0.004 moles is obtained. The mixture, containing about 9% of ethanol, is heated at a pH of 6.5. The pH value is adjusted by means of 0.5 n HCL. The temperature is increased to 68° C. within a period of about 3 hours, with uniform heat supply. Then, the liquid is cooled to 10° C. The suspension is further cooled and processed at a temperature of 10° C. The solution subjected to further processing contains from about 2 to 2.5% of albumin.

The enclosed drawing illustrates in schematic form the processing of the starting solution. In the process a modified rotating discharge filter type ZHF-S (Schenk, upright model) to accomodate the separation of a 600 l plasma batch within a maximum of 5 h filtering time was used. The central device of the complete system is a filter vessel 20, double walled to make both heating and cooling possible, having a capacity of about 220 l and a filtration surface area of about 3 m³. The circular filter discs 22 are sealed to a central rotating column 21 in such a manner that the filtrate, once having passed through the filter medium coating each disc, flows into the central column and then to the outlet through line 23 and valve 8. Removal of the residue (filteraid and precipitated globulins) between filtration cyclus is accomplished by centrifugal washing and a backwash of 1% NaCl, so that the filter is readily prepared for the next cycle. The filter element are covered with a metallic twisted (wire) or braid fabric.

The unfiltered starting solution is maintained in suspension within a slurry tank 24 with constant agitation (agitator 3). By means of a pump 2, the starting substance is introduced into the filter vessel 20 via the slurry feed value 10 through a pair of inlet valves 11, 12. The vessel may be pressurized with compressed air by means of compressed air valve 5.

Initially, the filter elements are precoated with filtering aid suspended in destilled water in a suspension of about 1 kilopond of Celite 545 (trademark for a kieselguhr filtering aid) in 500 milliliters of water, to form a primary precoat having a thickness of about 0.2 centimeters at atmospheric pressure. Thereafter, 500 liters of albumin-containing suspension are mixed with 25 kiloponds of Celite 545 and stirred. The mixture is introduced into the filter vessel from the slurry tank, and urged through the filter surfaces of elements 22 at a positive pressure of 2 bar (atmospheres). Prior to the actual dispensing of the liquid to the clear tank, the substance is repeatedly passed through the filter elements in the so-called recirculation process (recirculation valve 6, pump 2), until the filtrate appears to be sufficiently clear at the sight glass 25. Thereafter, the filtrate is discharged to the clear tank through valve 8.

As the clarified albumin containing solution leaves the filter, a 1% Na Cl wash solution is simultaneously pumped through the filter. (Volume of wash solution used is equal to half the volume of the original batch size). The filtration rate is 150 l/h. The protein concentration of the filtrate at the beginning of the process is about 2.5%, while the end concentration of non-albumin constituents is only about 0.05%. The resultant solution is clear with a protein concentration of about 1.5% albumin and an osmolality of approx. 1.000 mosm.

This clear filtrate is then diafiltered using the Millipore Pellicon Cassette system (filtration surface area 9.0 m³, Millipore GmbH, Neu-Isenburg, Germany). Diafiltration means, that the solution is filtered through a dialysis membrane. The flow rate at the beginning of the process is about 5-6 liters filtrate/min.

Operating on an 8-hours shift per day, the entire fractionation procedure takes 3 days.

day 1: Heat-ethanol precipation, subsequent cooling and pH 4.4 adjustment (5 hours), day 2: alluvial filtration (4 hours) and diafiltration (flow rate so regulated that process is finished at beginning of 3rd working day). The material is kept at temperatures between +6° C. and +8° C. by cooling the double walled vessels in both procedures, day 3: final adjustment of pH (7.0), protein concentration (5%, 20%), osmolality (300 mosm); clear filtration; sterile filtration (membrane 0.2 u); bottling; pasteurising (10 hours, 60° C.).

While the yield of albumin using the alluvial filtration/diafiltration procedure is 93% of the albumin present in the original starting material (average from 60 batches), and quality of the final product is the same as that achieved with previous methods, the greatest advantage of this methods lays in the fact that the entire process, with the exception of bottling, may be performed by one person.

Cleaning of the filters is effected by rotating the filter elements by means of the driving motor 1 and by discharging the slurry through discharge valve 9. Through valve 4, the discharged substance may be suspended and filtered again.

After its passage through the filter, the liquid does not show any Tyndall effect any longer, and it is clear as water. The liquid is free of accompanying substances, such as lipids or foreign proteins. The liquid may be used directly for the albumin concentration and subjected to to the subsequent filtration process In principle, the following steps incur the process:

PLASMA 600 kg:
33.6 kg PROTEIN
18.48 kg ALBUMIN (=55%)

1.

+9% ETHANOL
+0.004 M SODIUM CARPRYLATE

+HCL pH 6.5

2.

HEATPRECIPITATION: 30 min. 68° C.

3.

+HCL pH 4.4

4.

ALLUVIAL FILTRATION

FILTRATE

5.

DIAFILTRATION
5.1 CONCENTRATION
5.2 DIALYSIS

6.

+NaOH pH 7.0

7.

CLEAR FILTRATION

ALBUMIN SOLUTION 17.2 kg ALBUMIN (=93% YIELD)

EXAMPLE 4

From a placenta extract, the haemoglobin contained therein is initially removed with the aid of solvents, such as, for instance, trichloro acetic acid, chloroform, diethylether. Then, the protein-containing supernatant liquid is heated to a temperature of 68° C. at a pH of 6.5. Upon cooling and adjusting the pH to a value of 4.4 with the addition of 0.5 n HCl, 100 liters of the thus obtained liquid are mixed with 3 kiloponds of filtering aid and stirred (filtering aid: Hyflo-Super-Cel; trademark for a kieselguhr filtering aid).

At a temperature of 18° C. and a pressure of 4 bar (atmospheres), the liquid is urged through an alluvial filter of the above-specified type and having a mesh size of 70 microns. Accordingly, the operation is performed without a primary precoat. The liquid is passed in recirculation until it appears in the sight glass to be clear as water and free of the Tyndall effect. Thereupon, the albumin contained in the liquid is adjusted to the desired concentration by conventional methods.

After the entirety of the liquid has passed through the filter, the slurry retained in the filter is re-washed with destilled water or with 0.9% NaCl solution. The liquid in this manner is likewise clear as water, and it still contains from about 0.5 to 20% of albumin. This liquid may likewise be added directly to the albumin concentration.

Further reference may be made to the fact that the floating filtration may be carried out both with and without a primary precoat. Clearing of the filter elements is effected by rotation and countercurrent flushing the filter elements being rotated and the residues being discharged as slurry.

If a sufficient quantity of washing liquid is employed (namely distilled water or NaCl solutions), an increase of the yield of up to about 96% of the originally used quantity of albumin can be obtained. The quantities of impurities or turbidities (slurries)—caused by variation of the density ratio between solvent and solid substance as well as optimum mechanical distribution—as resulting in other separation processes, such as e.g. by centrifuging, particularly in the elution of the initially separated proteins, are avoided by residual volume filtration, either a cleaning of the volume of the filtering apparatus by rotation and countercurrent flushing or after a clearing thereof in the recirculation process has taken place. Filtration prior to the further processing of the diluted albumin solution may be dispensed with in view of the high degree of purity thereof.

The separation of solids is independent of temperature. The rate of filtration varies only slightly with increasing or decreasing temperatures, and such variation may be neglected. Normally, the heat-treated plasma acidified to a pH of 4.4 is subjected to separation at room temperature within a centrifugal purification filter adapted to be cooled by means of an external jacket. The filtration step may be performed at different temperatures as well. Experience has shown that a temperature range of from 4° to +40° C. can be applied as range of operation. Following the primary precoating which is performed almost without pressure, the filtration pressure may be increased to 4.0±2.5 bar (atmospheres). The resulting filtration capacity amounts to about 150 liters of filtrate per square meter per hour. As mentioned above, kieselguhrs prove to be of particular usefulness as filtering aids.

The quantities specified in the Example are variable depending on the capacity of the filter. Tests have been performed successfully, both with small volumes (about 10 liters) and in large vessels (about 500 liters).

EXAMPLE 5 and 6

Preliminary remarks:

Two currently discarded Cohn plasma fractions are known to contain albumin in amounts which might be economical to salvage if simple technique, like heating, would give an acceptable product. These fractions are fraction IV-1 and fraction IV. Fraction IV-1 is precipitated from Supernatant II–III at a content of alcohol of 19%, temp. −7° C., pH 5.2. The yield is about 20 to 25 grams of moist paste per liter of starting plasma, containing about 30% protein.

Fraction IV is precipitated from Supernatant II+III in two steps (first: Fraction IV-1 is won as above; two: alcohol is added to 40%, −6° C., pH 6.5, to bring down Fraction IV-4). The precipitates are removed together in a single centrifugation step as Fraction IV. Yield is 30 to 35 grams of paste per liter of plasma. Paste is 30% protein.

EXAMPLE 5

1.0 kg of FRACTION IV-1 paste is suspended with 2.0 L of water containing 0.004 M sodium caprylate stabiliser. The pH is adjusted to 7-7.5 with sodium hydroxide. The mixture is stirred gently at room temperature. pH is periodically checked and readjusted upwards. Most of the paste will dissolve within one hour. The resulting crude solution will contain about 10% protein and 4–5% alcohol and is adjusted to 9% alcohol.

The mixture is heated to 68° C. as described, and centrifuged. The precipitate is washed to remove entrapped albumin as described. The combined supernatants are filtered to clarify and precipitated with a suitable agent to collect the albumin.

EXAMPLE 6

Likewise, a suspension of 1.0 kg of Fraction IV paste in water containing stabilisers is dissolved similarly, using 3.0 L per kg for a final solution containing about 7.5% protein and about 7% alcohol. To experience, approx. 20% of the protein in Fraction IV-1 is albumin. If the above procedure is quantitative, 1 to 2 grams additional albumin might be recovered per liter of starting plasma. The yield of albumin from Fraction IV is in the same range.

Instead of the concentration of the albumin by PEG-recipitation and/or freeze-drying as specified in the examples, it is also possible to perform an ultrafiltration or a careful evaporation of the water of the solution by rotational evaporation.

If the concentration of the supernatant liquid produced after the globulin separation is effected by other methods than by albumin precipitation (e.g. by ultra-filtration, rotation—evaporation), the desired osmolality, the salt composition and the hydrogen ion concentration must be adjusted by dialysis with a corresponding liquid.

EXAMPLE 7

Methanol is added to 1 l of placental serum until the concentration of the alcohol has reached 10%; then sodium caprylate is added until its concentration has reached 0.003 M, (*) the pH is adjusted to 6.5 after which the mixture is held at this pH for 20 min. Then the pH is adjusted to 4.6 and the concomitant proteins and non-protein impurities are precipitated. The solution containing pure albumin is separated by centrifugation.

(*)the temperature is increased to 67.5° C. and maintained for 20 minutes.

EXAMPLE 8

Ethanol and sodium caproate are added to 1 l of placental serum until their respective concentrations have reached 8 and 0.004 M; the pH is adjusted to 6.3; subsequently the process is carried on in the manner described in Example 1.

EXAMPLE 9

Ethanol and sodium caproate are added to 1 l of placental serum until their respective concentrations have reached 7.5 and 0.003 M; the pH of the mixture is adjusted to 6.3; subsequently the process is carried on in the manner described in Example 1.

What is claimed is:

1. A method for the abstraction of pure serum albumin from blood plasma, blood products, and other bodily fluids or tissue extracts for use in therapy which comprises the steps of:

(a) separating the blood plasma from the solid constituents of the blood;
    (b) adding 0.001 to 0.1 moles of an albumin stabilizer;
    (c) treating with a lower aliphatic alcohol having the composition $(CH_3—(CH_2)_n—OH$, with n equal 0, 1 or 2 at a volume concentration of 7 to 4%;
    (d) said separating, adding, and treating steps being carried out at a temperature of from 60° to 75° C. and a pH from 4.5 to 7.5;
    (e) precipitating the concomitant proteins, partly or largely denatured; and
    (f) separating the resultant solution containing pure serum albumin from the precipitate at a temperature of 1° to 30° C.

2. A method according to claim 1, wherein the lower aliphatic alcohol is ethanol.

3. A method according to claim 2, wherein the content of alcohol is 8 to 12% by volume.

4. A method according to claim 1, wherein the albumin-stabiliser is sodium caprylate in a 0.003 to 0.005 mole concentration.

5. A method according to claim 1, wherein the pH-value of the treatment is 6 to 7.

6. A method according to claim 1, wherein the temperature is 67° to 69° C.

7. A method according to claim 1, wherein the solution containing pure albumin is separated from the precipitate by alluvial filtration through a fabric filter element, thereby collecting the non-albumin constituents together with a filtering aid on the filter elements and gaining a clear albumin-solution as a filtered product.

8. The process according to claim 7, characterized by performing said filtration within a centrifugal purification filter comprising a sealed pressure vessel, said filter elements having a mesh size of between 20 and 200 microns.

9. The process according to claim 8, characterized in that one of said filter elements has a mesh size from 70 to 90 microns.

10. The process according to claim 8, characterized by performing said filtration with horizontally disposed filter elements comprising metallic twisted (wire) or braided fabrics having a mesh size of 80 microns.

11. The process according to claim 7, characterized by mixing a suspension of from about 30 to 70 grams of kieselguhr filtering aid per liter.

12. The process according to claim 7, characterized by, that the clear albumin-solution is purified by diafiltration (filtration of water and known albumin constituents through a dialysis membrane).

* * * * *